United States Patent [19]

Bertleff et al.

[11] Patent Number: 5,107,015

[45] Date of Patent: Apr. 21, 1992

[54] PROCESS FOR THE PREPARATION OF 2-FORMYL-2-METHYL SUCCINATES

[75] Inventors: Werner Bertleff, Viernheim; Gerhard Butz, Offenbach, both of Fed. Rep. of Germany

[73] Assignee: BASF Aktiengesellschaft, Ludwigshafen, Fed. Rep. of Germany

[21] Appl. No.: 602,515

[22] Filed: Oct. 24, 1990

[30] Foreign Application Priority Data

Nov. 16, 1989 [DE]  Fed. Rep. of Germany ....... 3938092

[51] Int. Cl.⁵ .............................................. C07C 67/38
[52] U.S. Cl. .................................... 560/175; 560/176; 560/177; 562/517
[58] Field of Search ....................... 560/175, 176, 177; 562/517

[56] References Cited

U.S. PATENT DOCUMENTS 3,527,809  9/1970  Pruett et al. ......................... 568/451
3,917,661  11/1975  Pruett et al. ..................... 260/410.9

FOREIGN PATENT DOCUMENTS 1793069  2/1972  Fed. Rep. of Germany .

OTHER PUBLICATIONS

Kollár et al., *Chimia* 40, (1986), 428–429.

*Primary Examiner*—José G. Dees
*Assistant Examiner*—Vera C. Clarke
*Attorney, Agent, or Firm*—John H. Shurtleff

[57] ABSTRACT

The preparation of 2-formyl-2-methyl succinates by reacting itaconates with carbon monoxide and hydrogen in contact with a catalyst system comprising rhodium and a tertiary phosphorus compound, wherein the reaction is carried out under a pressure of from 90 to 325 bar.

6 Claims, No Drawings

PROCESS FOR THE PREPARATION OF 2-FORMYL-2-METHYL SUCCINATES

The present invention relates to an improved process for the preparation of 2-formyl-2-methyl succinates by reacting itaconates with carbon monoxide and hydrogen in contact with a catalyst system comprising rodium and a tertiary phosphorus compound at elevated pressure and temperature.

The hydroformylation of olefinically unsaturated compounds by the so-called low-pressure method involving the use of a catalyst system comprising rhodium and an excess of tertiary phosphorus compounds is generally known, as revealed, for example, by DE-OS 1,793,069. The recommended reaction conditions for this method are a temperature of from about 50° to 145° C. and a pressure of up to about 31.5 bar.

The preparation of 2-formyl-2-methyl succinates (Ia) and concomitantly the isomeric 2-formylmethyl succinates (Ib) from itaconates (II) by this method as indicated below:

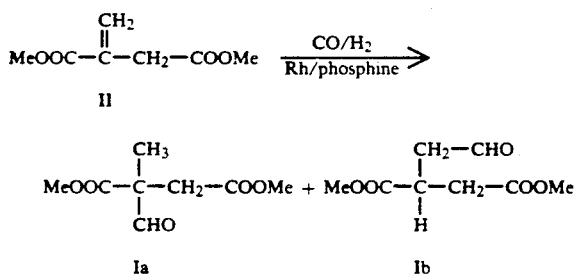

is the basis of work done by Kollár et al. [Chimia 40 (1986) 428], according to which the ester Ia is obtained in yields of from about 37 to 42% when using a rhodium/triphenylphosphine catalyst system at 100° C. and CO and $H_2$ partial pressures each of 40 bar (total pressure 80 bar). When using the optically active (4R,5R)-(−)-4,5-bis(diphenylphosphinomethyl)-2,2-dimethyl-1,3-dioxolane ["(R,R)-DIOP"], the yield if 73% under the same conditions, one of the optical isomers if Ia being formed in excess.

These unsatisfactory yields are due to the fact that up to 45% of the itaconate used is hydrogenated to methyl methylsuccinate in a side reaction. Only the use of the expensive "DIOP" can reduce the amount of methyl methylsuccinate to just 10%, but even in his case the yield of Ia is still unsatisfactory.

It is thus an object of the present invention to improve the availability of 2-formyl-2-methyl succinates by hydroformylation of itaconates.

Accordingly, we have found an improved process for the preparation of 2-formyl-2-methyl succinates by reacting itaconates with carbon monoxide and hydrogen in contact with a catalyst system comprising rhodium and a tertiary phosphorus compound at elevated pressure and temperature, wherein the pressure used is from 90 to 325 bar.

The good results achieved by this process are, as far as we have observed, virtually uninfluenced by the type of itaconate used, so that, in principle, any ester radical can be used. Since the products of the process will largely be used as synthesis components in the manufacture of polycondensates and polyadducts, during which the ester radicals are in any case eliminated, it is particularly preferred to use methyl, ethyl, benzyl and phenyl groups as ester radicals. Other possibilities are:

generally all $C_1$–$C_{10}$-alkyl groups and in particular $C_1$–$C_4$-alkyl groups,
generally all aryl groups,
generally all aralkyl groups and
cycloalkyl groups such as the cyclopentyl and cyclohexyl groups, which groups can themselves carry substituents which are inert to the reaction conditions, for example fluorine, chlorine and bromine, $C_1$–$C_4$-alkyl groups, $C_1$–$C_4$-alkoxy groups, the hydroxyl group, the cyano group and the nitro group.

According to the invention, the reaction is carried out under a pressure of from 90 to 325 bar, a pressure of from 100 to 280 bar and in particular from 100 to 160 bar being recommended. This total pressure is virtually the sum of the CO and $H_2$ partial pressures. The ratio of these partial pressures to each other and thus the molar ratio of CO to $H_2$ is preferably from 0.1:1 to 10:1 and more preferably from 0.8:1 to 1.2:1.

The process is in other respects the same as that normally used for the continuous or batchwise hydroformylation of olefinically unsaturated compounds using rhodium and tertiary phosphorus compounds as catalyst system, so that a detailed description thereof is not necessary here. The rhodium can be in the form of a complex, e.g. $HRh(CO)(PPh_3)_3$, or of any desired salt, particularly a non-halo salt. The rhodium (calculated as metal) is preferably used in an amount of from 100 to 400 mg per kg of itaconate.

The tertiary phosphorus compounds used are primarily triarylphosphines, especially triphenylphosphine, and alkyldiarylphosphines such as hexyldiphenylphosphine, but trialkylphosphines such as tributylphosphine and triaryl phosphites such as triphenyl phosphite and trialkyl phosphites such as triethyl phosphite are also suitable.

The molar ratio of these ligands to the rhodium preferably ranges from 20:1 to 500:1, more preferably from 40:1 to 250:1.

It is advantageous to carry out the hydroformylation at a temperature of from 50° to 150° C., especially at from 70° to 90° C., since only very small amounts of by-product occur at these temperatures.

The hydroformylation is particularly successful when carried out in the absence of a solvent, as in this case less trouble arises due to hydrogenation of the itaconate. If it is technically desirable to operate in the presence of a solvent, a suitable solvent is one which is inert to the reaction conditions, for example, toluene, xylene, dioxane or a carboxylate such as ethyl acetate or methyl succinate, used in an amount of from about 0.5 to 2 kg per kg of itaconate. Under the reaction conditions stated, the reaction time required for virtually quantitative conversion is from about 2 to 4 hours. The desired target product is usually obtained in a yield of from 70 to 85%. The final mixture also contains from about 1 to 10% of the isomer Ib and the remainder is mainly methyl succinate. All of these compounds can be separated by distillation in the usual manner.

The target products are important intermediates in the manufacture of plastics. Hydrogenation of the aldehyde function yields 2-hydroxymethyl-2-methyl succinate or 2-hydroxyethyl succinate, both of which are important synthesis components of polyesters. Perhydrogenation gives the corresponding triols, which are useful as cross-linking agents in the chemistry of polyesters and polyurethanes.

EXAMPLE

In a vertically stirred autoclave having a capacity of 2.5 liters a mixture of 700 g of dimethyl itaconate, 1.4 g of $HRh((CO)(PPh_3)_3$ and 15.7 g of $PPh_3$ was subjected to hydroformylation for 3 hours at 85° C. under a pressure of 100 bar exerted by an equimolar mixture of CO and $H_2$. The final reaction mixture was analyzed by gas chromatography, which gave the following yields:

| | |
|---|---|
| 2-formyl-2-methyl dimethylsuccinate | 81% |
| 2-formylmethyl dimethylsuccinate | 1.6% |
| 2-methyl dimethylsuccinate | 14.6%. |

We claim:

1. A process for the preparation of a 2-formyl-2-methyl succinate which comprises:
   reacting an itaconate with carbon monoxide and hydrogen in contact with a catalyst system comprising rhodium and a tertiary phosphorus compound at elevated temperature and under a pressure of from 90 to 325 bar.

2. A process as claimed in claim 1, wherein the reaction is carried out at a pressure of from 100 to 280 bar.

3. A process as claimed in claim 1, wherein the reaction is carried out at a temperature of from 50 to 150° C.

4. A process as claimed in claim 1, wherein the reaction is carried out at a temperature of from 70° to 90° C.

5. A process as claimed in claim 1, wherein the reaction is carried out under a pressure of from 100 to 160 bar.

6. A process as claimed in claim 1, wherein the reaction is carried out in the absence of any solvent.

* * * * *